United States Patent [19]

Solomons

[11] Patent Number: 5,009,847
[45] Date of Patent: Apr. 23, 1991

[54] KIT FOR DETERMINING BLOOD PLATELET STRESS

[76] Inventor: Clive C. Solomons, 164 S. Fairfax, Denver, Colo. 80222

[21] Appl. No.: 844,890

[22] Filed: Mar. 27, 1986

Related U.S. Application Data

[62] Division of Ser. No. 623,579, Jun. 22, 1984, Pat. No. 4,600,696.

[51] Int. Cl.$^5$ ................ C12Q 1/56; G01N 33/48
[52] U.S. Cl. .................................. 422/61; 435/13; 435/810; 436/63
[58] Field of Search ............ 436/63, 92, 98, 161; 422/61; 435/13, 29, 810

[56] References Cited

PUBLICATIONS

Solomons et al; Platelet Biochemistry and Function—Possible Use in Evaluating Biocompatibility, CA84(17):118071m, 1975.

Ericson et al; Plasma Concentration and Renal Excretion of Adenine and 2,8-Dihydroxyadenine After Administration of Adenine in Man, CA92(17):140398k, 1980.

Turturro et al; HPLC Method for the Separation of the Halogenated Pyrimidine 5-Bromo-2'-Deoxyuridine from its Metabolites; J. of Chrom., 252(1982), pp. 335-337.

Fisher Scientific 1983; Products catalog 1982, p. 115.

*Primary Examiner*—Barry S. Richman
*Assistant Examiner*—Lyle Alfandary-Alexander
*Attorney, Agent, or Firm*—Paul J. Cook

[57] ABSTRACT

A kit is provided for measuring chemical and physical stresses on the blood platelets of a human patient by measuring reduction in ATP (adenosine triphosphate) and ADP (adenosine diphosphate) concentrations while measuring increases in the ATP degradation products HYPX (hypoxanthine) and the AMP (adenosine monophosphate). The kit is useful for measuring a human patient's risk to internal stress such as reduction in the size of blood vessels, to response to various environmental changes as well as to a variety of treatments including drug treatment, risk of malignant hyperthermia in response to anesthetic administration or in response to vascular or organ transplant.

10 Claims, 1 Drawing Sheet

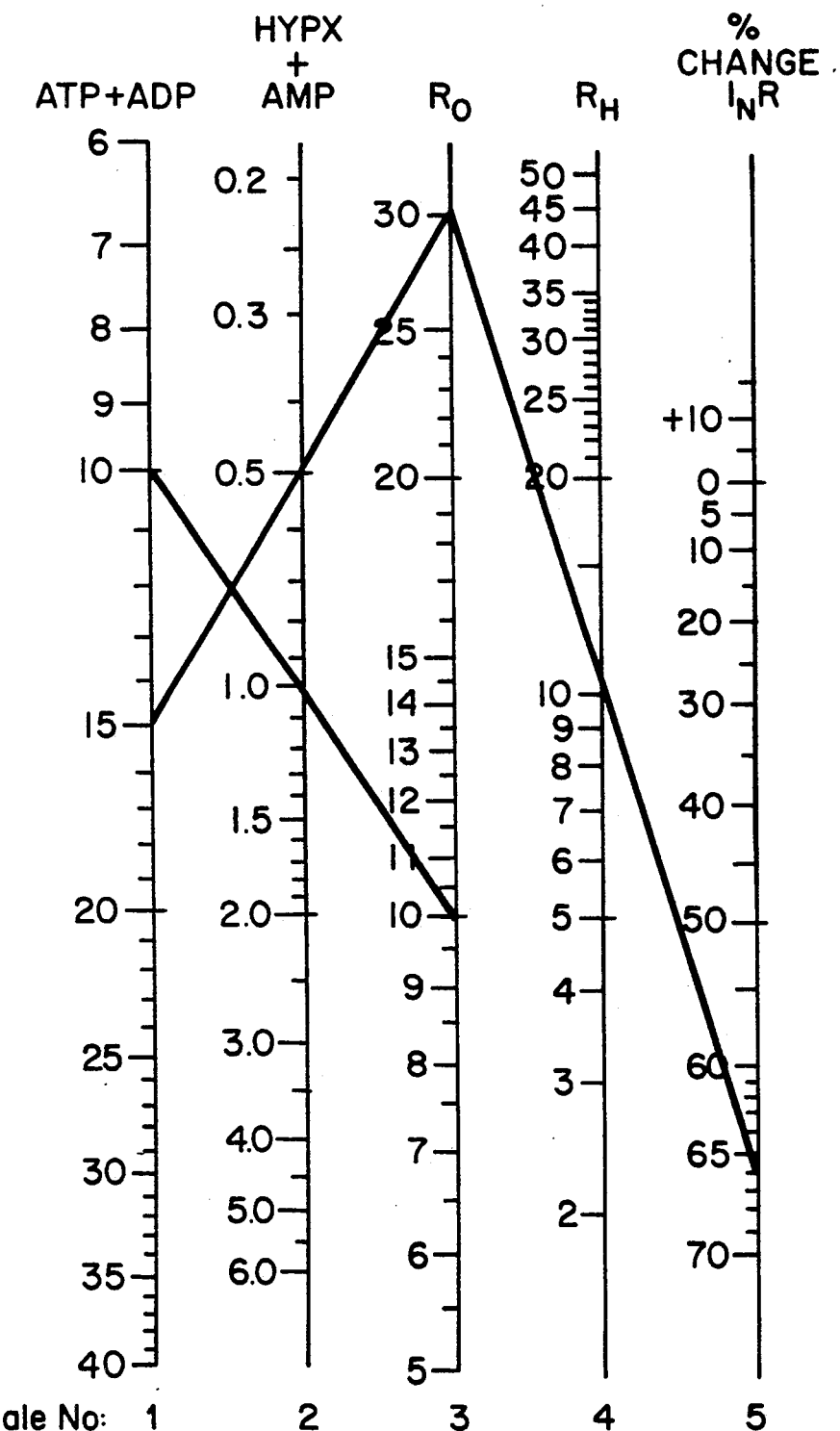

KIT FOR DETERMINING BLOOD PLATELET STRESS

This is a divisional of co-pending application Ser. No. 623,579 filed on Jun. 22, 1984 now U.S. Pat. No. 4,600,696

BACKGROUND OF THE INVENTION

This invention relates to a process for accurately measuring chemical and physical stresses on blood platelets of a human patient and for relating the measured stress to the effect of an outside agent to which the patient is exposed. More particulatly, the present invention relates to such a process and to a kit adapted to effect the stress measurement.

There are approximately 300,000 platelets per cubic mm. blood circulating in the blood stream. Platelets are derived from bone marrow cells and their most dramatic function is to prevent blood loss by forming a plug together with other blood products which stops the flow of blood from an injured vessel. Platelets are induced to aggregate to each other and to adhere to a cut or any foreign surface by metabolites such as ADP, thrombin and epinephrine, as well as by exposed collagen or atherosclerotic plaque in the walls of blood vessels. Changes induced by these agents cause platelets to release substances such as ADP into their immediate surroundings, thus affecting neaby platelets to follow suit. In this way a minor lesion in a blood vessel can accululate platelets and other debris eventually blocking the flow of blood. If the vessel is a coronary artery, the individual experiences a "heart attack". If the vessel is in the brain, a "stroke" results. Very often there is little warning of the impending catastrophy until the vessel is 80-90% occluded and alarming clinical symptoms suddenly become noticeable. Nevertheless, circulating platelets continually pass close to forming clots every two minutes and accumulate information indicative of progressive pathology before any symptoms are felt. Thus, the measurement of early stress reflected in platelets can lead to the institution of highly cost-effective preventative medical therapy to reduce the morbidity and mortality of thrombotic disease. Communicating with stressed platelets before they become irreversibly attached to a clot requires the creative use of technology to decode the internal cell language so that relatively undistorted messages can be registered and correlated with progression of the disease and the effectiveness of treatment.

The platelet like all other living cells uses ATP (adenosine triphosphate) as the most effective source of energy, whereby diverse forms of work can be purchased to maintain the status quo and synthetic output of the cell. ATP itself is made within the cell from simpler compounds such as glucose and amino acids. In the process of supplying energy, ATP is degraded, losing a phosphate group to become ADP (adenosine diphosphate). The process can be repeated forming AMP (adenosine monophosphate). Sustained mild stress of any kind causes the platelet to do more work to maintain itself and, consequently, this is reflected in a shift in the relative amounts of ATP, ADP and AMP, proportional to the degree of stress. With substantial, but not overwhelming stress, AMP is further degraded to HPYX (hypoxanthine). Hypoxanthine is salvageable to some extent to reform AMP which can also be converted back to ADP and hence, to ATP. Overwhelming stress can deplete the platelet of most of its ATP, converting it to a useless circulating body unable to function or causing it to aggregate to other platelets or foreign surfaces.

In addition to being the source of energy in cells, ATP and related compounds do double duty by functioning as conveyers of information to enzymes. Enzymes catalyse the chemical reactions of the cell and are modulated by substances such as ATP, ADP and C-AMP and other molecules and ions in accordance with instantaneous conditions of supply and demand. A disturbance in the communication process, which can occur when ATP/ADP ratios change, or calcium ions are uncontrolled, can lead to an inappropriate wastage of energy stores, a decay of the synchrony between integrated cellular functions and rapid irreversible damage.

The platelet has characteristics of metabolism which enables it to retain evidence of repeated insult in a more permanent fashion than a liver or muscle cell. This capability is due to the fact that the mature platelet, in contrast to other cells, is unable to make ATP from simple molecules, but must constantly recycle its supply of preformed adenine rings to make ATP or scavenge small amounts of circulating ring compounds. Thus, stresses which affect ATP metabolism are not easily or quickly forgotten by the platelet. This memory function is enhanced by the absence of DNA which in other cells is a source of information for repair functions and cell division. Because recycling of ATP and other functions are not totally efficient, normal platelets have a life span of 7-10 days.

A wide variety of outside chemical or physical stresses in the blood system of a human patient can cause the platelet chemistry to change in response to the stress. The condition known as malignant hyperthermia occurs in a small percentage of the population after being exposed to an anesthetic. Malignant hyperthermia is a genetic disorder in which agents such as succinylcholine and halothane can trigger a potentially fatal sequence of events which include acidosis, hyperkalemia, cardiac dysrhythmia, muscle rigidity and hyperthermia. Differences in the order in which symptoms are detected during a malignant hyperthermia episode and the wide variation of their expression at the time of anesthesia makes diagnosis difficult and adds complexity to genetic studies. The range of "triggering" agents has also been enlarged considerably in the light of clinical and experimental observations. Some patients who had previously received significant "triggering" doses of anesthetic without untoward incident, may have a florid malignant hyperthermia episode during subsequent anesthesia. In addition, malignant hyperthermia episodes under conditions of stress have occurred without general anesthesia and with local dental anesthesia. It would be desirable to provide a test to determine whether a patient is susceptible to malignant hyperthermia prior to administration of an anesthetic. Furthermore, it would be highly desirable to provide a means for testing a patient's reaction to physical or chemical stresses in general, including environmental conditions, the effect of drug treatment or the effect of organ or vascular transplant.

SUMMARY OF THE INVENTION

In accordance with this invention, a process and kit are provided for accurately determining the effect of chemical or physical stress on the blood platelets of a human patient. A sample of blood platelets free of red and white blood cells is obtained from a patient and is isolated and stored under conditions which avoid stress to the platelets. The platelets then are divided into subsamples including a control sample and at least one sample which is challenged by the chemical or physical stress for which the patient is being tested. The subsamples then are treated with a solvent for the nucleotides, ATP, ADP, AMP AND HYPX. The resultant solutions then are analyzed by chromatographic analysis to determine the relative concentration of ATP, ADP, AMP and HYPX in each sample. The kit comprising this invention includes containers having known concentrations of ATP, ADP, AMP and HYPX in order to permit forming of standard solutions that comprise a basis for the sample measurements. In one important aspect of this invention, the kit includes a container for an internal standard solution comprising a solvent for a standard nucleotide and the standard nucleotide. The internal standard solution can be injected into the chromatographic column to determine whether the column is functioning correctly. The kit also contains a positive control composition capable of inducing platelet stress as well as a standard solution of the composition or a surface composition for which the patient is being tested.

DESCRIPTION OF SPECIFIC EMBODIMENTS

In accordance with this invention, the reaction to chemical or physical stress on blood platelets of a patient is measured accurately and compared to a standard in order to determine whether a patient is at risk to a particular proposed treatment or to an environmental condition. The stress on the platelets can be due to conditions originating outside the body such as environmental conditions, drugs or anesthetics or the like or due to conditions in vivo such as the closing of one or more blood vessels which prelude strokes or heart attacks.

Platelets are easily, and safely, obtainable at minimal risk, by drawing blood from a vein. The ease of sampling platelets is contrasted by the danger of complications and expense associated with biopsies of muscle, liver, etc. Thus, it is of interest to know to what extent platelets resemble other cells so that observations made on platelets, if used intelligently, can provide insight into the functions of organs. For example, the use of platelets as a model for muscle has been very fruitful, and is supported by the structural components seen in platelets. Platelets possess actin and myosin and other proteins which are essential for the expression of contraction, as well as a membrane system capable of storing and controlling calcium ions, which are essential for the initiation of contraction, and the utilization of ATP. In reaction to chemical or physical stresses, platelets will change their shape, utilizing their internal contraction system as a prelude to aggregation and adhesion. Thus, if the correct plane of correspondence between platelets and other cells is identified, conclusions can be drawn and then checked that are valid for both cell types. Since cells are obviously not identical in all respects, the boundaries of meaningful correspondence can be defined by measurement.

In accordance with this invention, a blood sample is taken from a patient under conditions so that stress to the blood platelets is eliminated or minimized. Thus, the platelets should not be refrigerated or contacted with glass or scratched surfaces or centrifuged at excessive speed. In addition, vigorous stirring of the platelets is to be avoided. Conventional venipuncture is utilized to obtain the blood sample, but under conditions such that the needle does not touch the vein wall. The blood sample should flow directly into a container, the interior surface of which is coated with a composition that does not stress the blood platelets such as heparin or a heparin salt. The container utilized is not exposed to the atmosphere and is usually under vacuum just prior to the flowing of blood sample into it. The blood must not be refrigerated any time during the assay and should be maintained at a temperature between about 10° C. and about 30° C., preferably between about 15° C. and about 25° C. in order to minimize stress on the blood platelets. It is generally preferred not to employ citrate in the syringe as an anti-coagulant since the citrate will chelate calcium ions and thereby reduce sensitivity to the assay.

The blood platelets in each sample are obtained by centrifugation under conditions to minimize platelet reaction with the wall of the centrifugation tubes. It is preferred to use a bucket head centrifuge rather than a fixed angle centrifuge and to utilize low centrifugation speeds on the order of about 700 rpm to 900 rpm with a rotor diameter less than about 35 cm. After centrifugation, the supernatant should be inspected for physical contamination with red blood cells and, if so-contaminated, the sample should be respun for a short period, e.g., 3-5 minutes in order to clarify the supernatant. The supernatant then is recovered from the red blood cells and white blood cells and is transferred to a container having a surface composition that does not stress the platelets such as a polypropylene or polyethylene, so that samples of the platelets can be obtained conveniently. Samples of the platelets then are pipetted again under conditions which do not stress the platelets into a container which is to be mixed with a solvent for the nucleotides for which the test is to be conducted. Aliquots of the platelet-rich plasma having a platelet count of not less than about 200,000 per $mm^3$ and usually between about 300,000 to about 600,000 per $mm^3$ which constitutes a volume of between about 0.2 and 0.5 ml, preferably between about 0.3 and about 0.5 ml are pipetted into separate tubes for further treatment. Larger aliquots can be used, if desired.

In the instance where the blood platelets are to be challenged by a composition such as an anesthetic or a drug or any other composition to which the patient is to be exposed, one or more samples of the platelet-enriched plasma are incubated with the composition. Again, the mixing and incubation is conducted under conditions so as not to introduce physical or chemical stress other than that of the composition under test. Generally, the composition under test is introduced by syringe into the platelet-enriched plasma without touching the tube with the needle and thereafter swirling the tube gently in a water-bath maintained at the appropriate temperature. The incubation condition will vary with the composition or surface with which the platelets are stressed. Generally, incubation with a composition in solution is conducted for a period between about 15 and 30 minutes and at a temperature between about 35° C. and 40° C., preferably between about 36° C. and 38° C. After incubation, the containers in which the incubation is conducted are centrifuged so that the platelets form a pellet and the platelet-poor plasma is carefully removed such as by decantation or such as by syringe or needle and deposited into a container. A solvent for the nucleotides produced by the platelets then is added to the test sample. Suitable solvent compositions include 3 to 6% perchloric acid (PCA) in aqueous solution, PCA and methanol 3 to 6%, PCA and $KH_2PO_4$ in aqueous solution or the like. PCA with a preservative such as $KH_2PO_4$ or $NaPO_4$ are preferred solvent compositions since they can be stored for extended times. These solvent compositions are capable of dissolving AMP, ADP, ATP and HYPX as well as other nucleotides. The resultant composition is agitated by any convenient means, allowed to sand in ice at a temperature between about 1° C. and about 0° C. in order to complete the extraction. Centrifugation is conducted in order to remove the proteins and cell debris. The supernatant is maintained at a temperature of less than about −18° C. and preferably between about −30° C. and about −70° C. and then is analyzed for adenine nucleotides. Analysis can be conducted by any conventional means including bioluminescence or high performance liquid chromatography (HPLC) processes.

When utilizing HPLC, this invention provides a unique kit that affords efficient and accurate sample analysis. Test and control samples are introduced into the chromatographic column and the peak height of the constituent nucleotides is measured in order to determine individual nucleotide concentration. A conventional salt such as $KH_2PO_4$ or $NH_4H_2PO_4$ can be added to the sample in order to maintain the correct ionic strength. In an important aspect of this invention, internal standard compositions are provided so that the chromatographic column can be standardized and so that the column can be monitored to determine whether it is functioning properly. The standard compositions are conveniently added to the solvent compositions so that they can be conveniently mixed with the sample in one step and provide an internal standard for the column. The internal standard composition comprises a known concentration of a nucleotide which is not a cell metabolite such as deoxyuridine, adenine, thymine, guanine, uridine or cytosine which elute from a chromatographic column separately from ATP, ADP, AMP or HYPX. Deoxyuridine or adenine are preferred internal standard compositions. The internal standard provides a direct measure of whether the sample has been injected properly into the column and/or whether the column is functioning properly. This is easily determined by monitoring the size of the peak obtained from the chromatograph for the internal standard. If the peak deviates significantly from that which should have been obtained with the known concentration of the internal standard, then it is known that the chromatographic results obtained with that particular sample should be disregarded.

In one aspect of this invention, a kit is provided which includes one or more containers for a standard composition containing ATP, ADP, AMP, HYPX or mixtures thereof. The standard compositions preferably are in solid form either alone or admixed with a buffer preservative such as $KH_2PO_4$ in known concentration. When used to standardize the chromatographic column, they are dissolved in a solvent, e.g., aqueous PCA and injected into the column to obtain standard peaks. Alternatively, UA and/or XA can be included in these standards because they can occur in the PCA extract as a result of plasma entrapment in the platelet pellets and give rise to peaks in the chromatogram.

The kit also includes a positive control composition which is known to stress blood platelets. The positive control provides a measurement of relative concentrations of AMP, ATP, ADP and HYPX in a sample stressed with a known concentration of the positive control and thereby provides a contrast measurement showing that the sample platelets are functioning normally or not functioning normally. Suitable positive control compositions are those that stress the cell membrane such as dinitrophenol or a detergent such as sodium dodecyl sulfonate (SDS) or the like in aqueous solution, e.g. 10 gm/100 ml SDS. The kit also includes a plurality of vials having their internal surface coated with a composition that does not stress platelets. Suitable coatings include polyethylene, polypropylene or silicone. The preferred vials are those formed of polyethylene or polypropylene.

In an alternative embodiment, the kit can include a blunt ended pipette designed to avoid stress to the blood platelets. Optionally, the kit also can include a nomograph shown in FIG. 1 which provides a convenient means for determining the ratio:

$$R = \frac{ATP + ADP}{AMP + HYPX}$$

The nomograph will be described with reference to testing with halothane anesthetic. The first column labeled ATP+ADP comprises a logarithmic scale, base 10, ranging between the numbers 6 and 30. The second column labeled HYPX+XA comprises a logarithmic scale, base 10, ranging between the numbers 0.1 and 3.0. The number 0.5 of the second column is aligned with the number 10 of the first column. The sums of the peak heights from the chromatographic column are determined and the appropriate determined numbers of the first and second columns are aligned with a straight edge. The point at which the straight edge intersects the third column labeled with the ratio is the numerical value of the ratio. The fourth column is the R value obtained as above for platelets exposed to halothane. This value is joined to the R value obtained without halothane on column 3 and the line extended to intersect column 5. The value on column 5 is the % reduction in R due to halothane, i.e. $[100-(R_H/R_O)\times100]$. The use of the nomogram of FIG. 1 is illustrated by the following example. If a platelet sample unexposed to halothane produces a measurement on HPLC of ATP+ADP of 15 cm and AMP+HYPX of 0.5 cm, then $R_O=30$. If a platelet sample exposed to halothane produces a measurement on HPLC of ATP+ADP=10 cm and AMP+HYPX of 1.0 cm, then $R_H=10$. The percentage decrease in R due to halothane is:

$$100 - \left(\frac{R_H}{R_O} \times 100\right)$$

$$100 - \frac{10}{30} \times 100 = 66\%$$

In using the nomogram, join point 15 on scale 1 to point 0.5 on scale 2 and read off answer, $R_O=30$ on Scale 3. Thereafter, join point 10 on scale 1 to point 1.0 on scale 2 and read off answer, $R_H=10$ on scale 3. Lastly, join point 30 on scale 3 to point 10 on scale 4 and read off answer % decrease in $R=66\%$ on scale 5. $R_H$ is obtained with halothane. $R_O$ is the control.

Optionally, the kit also can contain a sample of known concentration of the composition for which the platelet stress test is to be conducted. In the case of a malignant hyperthermia test, this sample can comprise the anesthetic to which the patient is to be subjected. In one particular aspect of this invention, it has been found that a mixture of (a) halothane and (b) dinitrophenol $10^{-2}$M or a 10% aqueous mixture of sodium dodecyl sulfonate at a volume ration of a to b between about 0.1:1 and 0.5:1 is particularly useful in testing for stress by the halothane because it reduces the ATP content of the platelet and provides evidence of viability of the platelet.

The platelet nucleotide assay of this invention is very useful because it yields pertinent information about metabolic risk safely and without appreciable discomfort. Since only a small volume of blood is required, the assay can be used repeatedly on children or adults in order to estimate risk at the time of each exposure to the composition under test such as an anesthetic. In the case of an anesthetic, the problem of periodic exacerbation of MH-associated indicators previously noted for plasma DPK can thus be circumvented.

In testing for an in vivo abnormality such as a suspected heart attack or a stroke, blood samples are obtained from the patient and treated as set forth above to recover platelet-rich plasma samples. The samples are extracted with a solvent for AMP, ADP, ATP and HYPX which also contain the internal standard and the extracts are processed by HPLC. The measured AMP, ADP, ATP and HYPX are the compared to previously established standards obtained with normal patients to determine blood platelet stress. High platelet stress is indicative of heart attack or stroke.

A value for $100-(R_H/R_O\times 100)$ of 60% or greater shows that the patient is experiencing an abnormality in vivo or is reacting abnormally to an outside agent.

The following examples illustrate the present invention and are not intended to limit the same.

EXAMPLE I

Methods and Materials

Patient selection: There were 26 normal patients (Group I), 14 patients having a clinical history of MH (Group II), 8 patients having a clinical history of MH and a positive contracture muscle biopsy (Group III) and 10 patients having a muscle or metabolic disease without having MH (malignant hyperthermia), i.e., myotonic dystrophy, osteogenesis imperfecta, hyperthermia, hyperkalemia, acidemia (Group IV). Criteria for a clinical episode of MH were respiratory and metabolic acidosis, dysrhythmias and hyperthermia.

Preparation of Platelet-Rich Plasma

Platelet nucleotides are stable provided the platelet is not unduly stressed by mechanical and chemical factors. The requisite conditions for technical success as well as the more common errors associated with manipulation of the platelets are listed in the Appendix.

The skin adjacent to a peripheral vein was swabbed with pure ethanol and allowed to evaporate. A tourniquet was lightly applied and 1-5 ml blood removed into a Vacutainer ® tube and discarded. For the assay, 7-10 ml of blood was drawn into a 10 ml Vacutainer ® coated with heparin. The tube was inverted gently 4 times, the stopper removed and the tube centrifuged relatively slowly in a bucket type machine at room temperature (30 cm diameter rotor at 800-900 rpm). The supernatant platelet-rich plasma (PRP), free of red and white cell contamination, was transferred using a Selectapette ® (Clay-Adams, Parsippany, NJ, 07054) and plastic tip, to 5 ml Falcon ® high molecular weight polypropylene tubes (75 mm × 10 mm) which were capped and mixed once by inversion. Aliquots of 0.4 ml PRP having a platelet count of not less than 200,000/mm$^3$ and usually 300,000 to 600,000/mm$^3$ were pipetted into two 5 ml Falcon ® tubes.

Addition of Halothane and Incubation 5 microliters (5 ul) of halothane (Ayerst) were drawn into a Hamilton syringe and dispensed under the surface of the PRP without touching the bottom of the tube with the needle. Each tube was capped within 2 seconds, the contents briefly mixed by swirling the tube, and placed in 37° C. waterbath for 20 minutes. The tubes were centrifuged with their caps in place for 2.5 minutes at 3000 rpm in a fixed angle Serofuge ® (Clay-Adams, Parsippany, NJ, 07054). The platelets formed a pellet on the side of the tube near the bottom allowing for the removal on the platelet-poor plasma by a carefully placed syringe and needle. The pellet should be free of visible contamination with red blood cells.

Extraction of Nucleotides

The nucleotides were extracted for assay in the following manner. The tubes were placed in an ice bath and 0.1 ml of cold (0°–4°) perchloric acid (PCA) (6 ml concentrated PCA diluted with 94 ml H$_2$O) is added. An internal standard of 2-deoxyuridine, 10 microgram/ml of PCA can be utilized. The tubes were agitated with a vortex shaker (5 secs) and allowed to stand in ice for 5-10 minutes before being centrifuged for 2.5 minutes at 300 rpm in the Serofuge ®. The PCA supernatant was kept at 0° C. or less and analysed for adenine nucleotides.

HPLC Analysis

Waters Associates (Milford, MA, 01757) HPLC equipment was used isocratically with the detector set at 254 nm. 5-20 ul of the PCA extract was injected onto a C-18 microbondapak column and phosphate buffer was pumped through the steel jacketed column at 2 ml/min or 4/8 ml/min for the radial compression module (RCM). The buffer was aqueous 0.1 mol/L KH$_2$PO$_4$ or 0.1 mol/L NH$_4$H$_2$PO$_4$, the latter being recommended, without any pH adjustment for either buffer. The peaks emerged from the chart recorder in the order ATP, ADP, uric acid (UA), HYPX, Xanthine (XA), MAP and Deoxyuridine (DOU) and their heights were linearly proportional to their concentration. Identity of peaks was established both by co-chromatography of known standards and specific enzymatic reactions.

Calculation

Peak heights (cm) were used to calculate the R value of both the control sample (R) and of the sample exposed to halothane ($R_H$) by the following formula:

$$R \text{ or } R_H = \frac{ATP + ADP}{AMP + HYPX}$$

The reduction in the R value is calculated as:

$$\% \text{ Reduction in } R = \left[1 - \frac{R_H}{R}\right] \times 100$$

The decrease in the R value must be accompanied by appreciable decreases in ATP and ADP and not be due to an increase in AMP and HYPX alone.

An F test and two-tailed student t test were used to compare the (Table 1). Analytical reproducibility and recovery were consistently in the range of 95–105%.

Results

The results are summarized in Table 1. The 8 patients with positive muscle biopsy contracture test had a mean percentage reduction in R of 76.1±4.7 SEM and the 14 clinically diagnosed patients had a mean percentage reduction in R of 74.1±3.4 SEM. There was no statistically significant difference between these two groups which were combined to give a mean percentage reduction in R of 74.9±2.7 SEM. The mean percentage reduction in R was 20.5±4.7 SEM for the 26 normal patients and 15±7.8 SEM muscle and metabolic disease patients. The latter two groups were not statistically different from each other. When the means of the normal subjects were compared with those of clinically diagnosed MH patients, the difference was highly statistically significant. Therefore, those individuals whose percentage reduction of R was less than 60% are judged to be at statistically insignificant risk for exposure to halothane; this cut-off point was adopted as it is more than 2 standard deviations less than the MH mean.

These results were supported by a completely independent evaluation of 15 clinically documented MH patients (3 of whom had a positive muscle contracture test). In all 15 patients the decrease in the R value was greater than 60% (mean 69.6±1.85 SEM) (Masson, NC, 1982 unpublished observations.

The following technical guide lines are useful in obtaining consistent results with the PHB. Common pitfalls and lapses in technique are described which were observed during visits to a number of laboratories evaluating the assay. These comments are particularly directed to those with limited experience in handling platelets, and in our view, they are crucial to obtaining accurate results. Briefly, all the technical steps in the assay should be designed to avoid damaging the platelets or the surface of the receptacles in which they are handled. Damage occurs to platelets when they are refrigerated or placed in contact with glass or scratched surfaces or centrifuged at excessive speeds. Shaking is generally quite well tolerated, but vigorous stirring is to be avoided. Arterial and venous blood are equally suitable for analysis. It should be noted whether the patient has received dantrolene sodium or other medications likely to change the expression of MH during the 10 days prededing the test.

The criteria for precise methodology require that at least 20 normal controls who have not had chronic exposure to anesthetic gas or industrial chemicals and 6–12 MH patients whose episodes were fully documented, as well as several relevant diseases, should be tested before reporting an unknown.

Venipuncture a. Swab with ethanol or isopropanol only and allow to dry.

b. Use needle no smaller than #22 gauge.

c. Discard first 1–2 ml to remove thromboplastins.

d. Do not allow the needle to touch the vein wall.

e. The blood should flow directly into a heparinized Vacutainer ® at a rate not slower than 5 ml/20 sec.

f. The Vacutainer ® should contain Na or Li heparinate evenly distributed. Tubes with powdered anticoagulant are not suitable, nor are tubes which contain glass mixing beads even if the beads are discarded before use.

g. Blood should not be placed in previously used plastic tubes since scratches and traces of detergent can affect platelets.

h. The blood must not be refrigerated at any time during the assay.

i. Buffered citrate placed in the syringe may be used as the anticoagulant, but some sensitivity may be lost due to chelation of calcium ions.

Centrifugation a. The centrifuge used to prepare PRP should have a bucket head, not the fixed angle type in order to minimize platelet reaction with the wall of the tube. Speed control at low speeds required is difficult to obtain with large machines having a rotor diameter larger than 35 cm. Refrigeration must be avoided during centrifugation.

b. After centrifugation, the PRP should be inspected for visible contamination with RBC and respun for 3–5 minutes if necessary.

Addition of Halothane a. Pipettes with plastic or glass tips must not be used to transfer halothane to PRP. A glass microliter syringe, preferably with a "blunted" metal needle is used. The needle is placed below the surface of the PRP without touching the bottom of the 5 ml Falcon ® tube. Other types of tubes, particularly those with cone shaped bottoms, should not be used.

Incubation of PRP+Halothane at 37° C.

a. Incubation must be done in a waterbath, rather than in an air bath in order to ensure constant temperature.

b. Occasional agitation at 5 minute intervals is permissable, but vigorous mixing or shaking must be avoided.

c. The caps must be tight fitting. Labels on the tube should be placed so as not to interfere with the seal.

Centrifugation Post-incubation a. A serofuge or fixed angle centrifuge is used after incubation so that the platelet pellet adheres to the side of the tube near the bottom facilitating the removal of the plasma without distrubing the pellet.

Perchloric Acid Addition and Extraction a. PCA should be cold (0°–5° C.) and not have any turbidity and a fresh tube of PCA should be used after every 10 samples.

b. The PCA extract after the final centrifugation should be clear. Turbidity at this stage indicates that the removal of plasma after incubation was incomplete and the run must be discarded.

c. The PCA extract must be kept ice cold or below. The tube containing this extract must not be placed on the pump head of the HPLC apparatus or in the draft of the instrument fan as this will warm the extract and result in decreased ATP content.

d. The PCA extract can be stored at −20° C. or below, but the temperature of the freezer must be checked regularly with a thermometer and the refrigerator should not be opened frequently.

e. The addition of methanol, trichloracetic acid or charcoal for extraction of the nucleotides is not recommended and complicates the assay unnecessarily.

f. Neutralization of the PCA is not needed at the concentration and temperature used. The PCA does not interfere with subsequent HPLC analysis.

HPLC Analysis a. When the overlap between ATP and ADP peaks is more than 20% of the height of each peak, the column is loosing its resolving power and should be renewed.

b. pH of the mobile phase should be checked to ensure that the correct salt has been used (pH approx 4.7).

c. Drifting of the baseline occurs when the PCA is contaminated or the column is infected with bacteria and mold.

d. Peak height is recommended rather than peak area as a measure of concentration because small baseline variations have a considerable effect on the areas of the sharp, highly resolved peaks that are characteristic of HPLC technique.

e. If enzymatic or tachyphoretic assays are used instead of HPLC, the effect of halothane and PCA on these systems must first be determined.

TABLE 1

PLATELET-HALOTHANE BIOASSAY
STATISTICAL ANALYSIS OF DATA

| Variable | # of Cases | Mean | Std. Dev. | Difference | p-Value |
|---|---|---|---|---|---|
| Patients |  |  |  |  |  |
| % Reduction in R |  |  |  |  |  |
| Group II | 14 | 74.1 | 13.1 | 2.0 | NS |
| Group III | 8 | 76.1 | 13.2 |  |  |
| Controls |  |  |  |  |  |
| % Reduction in R |  |  |  |  |  |
| Group I | 26 | 20.5 | 23.8 | 5.5 | NS |
| Group IV | 10 | 15.0 | 24.8 |  |  |
| % Reduction in R |  |  |  |  |  |
| Group I | 26 | 20.5 | 23.8 | 54.4 | .0001° |
| Group II and III | 22 | 74.9 | 12.9 |  |  |

Group I = Normal Subjects
Group II = Clinically Diagnosed MH Patients
Group III = Positive Muscle Biopsy patients
Group IV = Metabolic Disease patients
*Statistical Significance

EXAMPLE II

This example illustrates the use of a kit of this invention adapted to measure susceptibility to malignant hyperthermia as a result of halothane administration. A 10 ml blood venipuncture is introduced into a polypropylene Vacitainer® and stored at room temperature for less than 3 hours. The blood sample is centrifuged at 800 rpm at room temperature (22° C.) to obtain platelet-rich plasma (PRP) as the supernatant. The RPR is placed in a polypropylene tube (tube A) using a blunt end plastic tip pipette. A small aliquot (50 ul) is removed for platelet count which should be above 200,000/mm$^3$. Aliquots of 0.4 m. PRP are placed in three polypropylene tubes (tubes B, C and D) using a plastic tip pipette.

To tube B, nothing is added to the PRP and it is capped to form the control sample. To tube C is added 5 ul halothane, mixed and capped. To tube D is added 5 ul halthane and 10$^{-2}$M dinitrophenol as a positive control to induce platelet stress which is then mixed with the PRP and capped. If sufficient PRP is available, duplicates of tubes B and C and prepared. Each tube, B, C and D, is incubated at 37° C. for 15 minutes in a water-bath. After removal from the water bath, each tube is gently shaken to mix and then centrifuged at 2500 rpm for 3 minutes. The supernatant is removed by decantation and discarded. To the platelet pellet in each tube is added 0.2 ml and 3% aqueous PCA which then is mixed and centrifuged at 2500 rpm for 3 minutes.

The clear PCA supernatant from tubes B,C and D is placed in in plastic centrifuge tubes on ice using a pipette. The precipitate is not disturbed and the treated tubes are labeled b, c and d corresponding to tubes B, C and. The supernatant can be stored for batched HPLC runs at −20° C. to −70° C. for up to about 3 days.

For HPLC analysis, a buffer solution is produced to equilibrate the chromatographic column in a conventional manner. A vial labeled (S) contains a solid mixture of ATP $0.5 \times 10^{-3}$ (g), ADP $0.5 \times 10^{-3}$ (g), AMP $0.5 \times 10^{-3}$ (g) and HYPX $0.5 \times 10^{-3}$ (g) in KH$_2$PO$_4$ $50 \times 10^{-3}$ (g) to which is added 1 ml of water to form a standard composition, 20 μl of which is suitable for injection into the chromatographic column to produce a standard chromatogram. Twenty microliters of each PCA supernatant which contain deoxyuridine as the internal standard from vials b, c and d are injected into the chromatographic column. The column is run until the internal standard is eluted and compared to the previously standardized internal standard. If the internal standard and previously established standard match, the detector is set at 254 nm and the remainder of the sample is eluted to produce the chromatogram. The R and R$_H$ are calculated as set forth above. A decrease of more than about 60% for R shown significant platelet stress as a result of halothane exposure.

Results are not reported since they would be inaccurate when:

1. Venipuncture was traumatic, blood was hemolyzed or previously refrigerated or shows evidence of clotting.

2. The platelet count was below 200,000/mm$^3$. In that event, venipuncture technique, age of vacutainer tube should be checked. Blood from indwelling catheters is unsuitable.

3. PCA was turbid after centrifugation. Check technique of removing plasma.

4. If ATP peak heigt in positive control (tube D) was higher than ATP in tube B.

5. Standards not adequately separated by HPLC. Overlap of ATP and ADP peaks should not be greater than 40% of the peak height of ATP 6. Internal standard varies by more than 20% between runs. Check injecter.

7. If R value for tube B is less than 8.0, check for traumatic venipuncture, clotting, stressful environmental conditions.

8. If uric acid peak is greater than ATP peak indicating incomplete removal of plasma or unusual metabolic disorder.

I claim:

1. A kit for determining physical or chemical stress on blood platelets by measuring the relative concentration of adenosine tryphosphate, adenosine diphosphate, adenosine monophosphate and hypoxanthine in a sample of platelet-rich plasma containing an anticoagulant selected from the group consisting of heparin and a heparin salt which comprises:

at least one standard container containing known concentrations of at least one of adenosine triphosphate, adenosine diphosphate, adenosine monophosphate and hypoxanthine, a second container containing a known concentration of an internal standard nucleotide and at least two sample containers coated with a composition that minimizes or prevents chemical or physical stress in blood platelets a third container for a blood sample coated with an anticoagulant selected from the group consisting of heparin and a heparin salt, and nomogram shown in the Figure and defined by the algorithm $$R = \frac{ATP + ADP}{AMP + HYPX}.$$

2. The kit of claim 1 which includes a pipette having an open blunt end adapted to minimize physical stress on blood platelets.

3. The kit of claim 1 wherein said standard container contains adenosine triphosphate, adenosine diphosphate, adenosine monophosphate and hypoxanthine.

4. The kit of any one of claims 1, 2 or 3 wherein said at least one standard container further contains uric acid and xanthine.

5. The kit of any one of claims 1, 2 or 3 wherein said internal standard nucleotide is deoxyuridine.

6. The kit of any one of claims 1, 2 or 3 which includes a fourth container containing a known concentration of a positive control composition to which blood platelets are to be exposed to effect platelet stress at a known level.

7. The kit of any one of claims 1, 2 or 3 which includes a sample of a solid surface to which blood platelets are to be exposed to determine platelet stress response.

8. The kit of any one of claims 1, 2 or 3 wherein said internal standard nucleotide is adenine.

9. The kit of any one of claims 1, 2 or 3 which includes a sample of a solution of a test composition to which blood platelets are to be exposed to determine platelet stress response.

10. The kit of any one of claims 1, 2 or 3 which includes a test solution containing halothane to which blood platelets are to be exposed to determine platelet stress response.

* * * * *